(12) United States Patent
Pronk

(10) Patent No.: US 6,907,104 B2
(45) Date of Patent: Jun. 14, 2005

(54) COMPUTER-CONTROLLED X-RAY IMAGING DEVICE

(75) Inventor: Bernardus Johannes Pronk, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/477,565

(22) PCT Filed: May 15, 2002

(86) PCT No.: PCT/IB02/01680
§ 371 (c)(1),
(2), (4) Date: Nov. 13, 2003

(87) PCT Pub. No.: WO02/093986
PCT Pub. Date: Nov. 21, 2002

(65) Prior Publication Data
US 2004/0170251 A1 Sep. 2, 2004

(30) Foreign Application Priority Data
May 16, 2001 (EP) .......................................... 01201839

(51) Int. Cl.$^7$ ........................................... G01N 23/083
(52) U.S. Cl. ........................... 378/62; 378/98; 378/901
(58) Field of Search ............................. 378/4, 21, 62, 378/98, 162, 165, 901

(56) References Cited

U.S. PATENT DOCUMENTS

| | | | |
|---|---|---|---|
| 3,932,759 A | | 1/1976 | Brundin |
| 5,588,036 A | | 12/1996 | Fujise et al. |
| 5,737,386 A | | 4/1998 | Strawder |
| 5,986,662 A | | 11/1999 | Argiro et al. |
| 6,243,441 B1 | * | 6/2001 | Zur .......................... 378/98.8 |
| 2002/0079458 A1 | * | 6/2002 | Zur ....................... 250/370.11 |
| 2004/0147840 A1 | * | 7/2004 | Duggirala et al. .......... 600/437 |
| 2004/0193022 A1 | * | 9/2004 | Torii et al. .................. 600/300 |

FOREIGN PATENT DOCUMENTS

DE 196 25 410 A1 1/1998

* cited by examiner

Primary Examiner—David V Bruce
(74) Attorney, Agent, or Firm—Fay, Sharpe, Fagan, Minnich & McKee LLP

(57) ABSTRACT

The invention relates to an X-ray examination device which is designed to automatically process one or a series of X-ray examinations. The automatic processing in this device relates to all phases of the examination and includes the setting of the power of the X-ray equipment, the setting of the parameters of the X-ray table, the type of examination to be performed, and the reporting and archiving functions.

The apparatus in accordance with the invention also takes into account data which is specific of the patient to be examined, for example, the identity, the weight of the body and the part of the body to be examined.

6 Claims, 1 Drawing Sheet

COMPUTER-CONTROLLED X-RAY IMAGING DEVICE

The invention relates to a computer-controlled device for forming an X-ray image or a fluoroscopic image or the like, which device includes a computer and components which are connected to the computer and are selected from a group of components which includes an X-ray source, a collimator, an examination table, a detector, an image processing member, at least one monitor, a user interface, an archiving member and a printer, said computer being provided with a database for the storage of settings of the X-ray source and of the examination table and with a control member for carrying out such settings which are taken up in the database. It is to be noted, however, that a device of this kind may also be arranged for the execution of an examination by means of ultrasound.

A device of the kind set forth is known from DE-A 19 625 410.

The known device provides the setting of the X-ray source and the examination table in dependence on user-specific preferred settings. Such preferred settings may be stored, for example, on a chip card which can be introduced into a reading device for such a chip card, after which the X-ray source and the examination table can be adjusted in conformity with the preferred data.

U.S. Pat. No. 3,932,759 discloses a device for carrying out X-ray examinations in which the setting of parameters which are of relevance to the X-ray exposure, for example, the radiation intensity, is preprogrammed as a function of the organ of a patient to be examined.

It is a drawback of such a known device that, despite the long felt need to facilitate the task of the user of the device, numerous actions are required still so as to carry out a patient examination.

It is an object of the invention to improve this situation and to facilitate the task of a user of the device of the kind set forth in the preamble.

It is a further object of the invention to optimize the use of the device by reducing the amount of time required to carry out an X-ray exposure or the like on a patient.

It is another object of the invention to reduce the personnel required for the use of the device.

It is a further object of the invention to improve the control of the formation of X-ray images or fluoroscopic images by means of such a device, resulting in a high degree of reproducibility which is independent of the user of the device to a significant extent.

It is another object of the invention to improve the information traffic in the hospital environment in which the device is installed.

To this end, in conformity with a first aspect of the invention, the device is characterized in that the database contains patient-specific data and examination-specific data, and that the computer is arranged to execute a predetermined examination program in dependence on the patient-specific data and the examination-specific data taken up in the database, the control member carrying out, in dependence on the patient-specific data and the examination-specific data taken up in the database, the setting of the components selected from the group of components.

The patient-specific data preferably concerns information regarding identity, physical features and the parts of the body of the patient to be examined. The examination-specific data will preferably concern data relating to the time of examination, desired presettings of the X-ray source, of the detector and of the examination table, and to the examination program to be executed.

An examination can thus be executed in a practically completely automated fashion; it is to be noted that in this context the term "examination" is to be understood in a broad sense. An examination of this kind includes essentially an acquisition phase in which one or more images of the patient are formed, a reviewing phase in which the images formed are reviewed, and a printing or archiving phase in which a selection of the images formed is printed so as to be evaluated by a radiologist and in which storage of a selection or of all images takes place in archives which are usually of the electronic type.

Preferably, the computer is arranged to draft, in dependence on the predetermined examination program, a report which contains a selection of the images obtained. The reporting as part of an examination can thus also be drafted in a manner which is automated to a high degree, so that the user merely has to draw conclusions from the examination data taken up in the report.

During the execution of the examination phases, the computer-controlled device in accordance with the invention optionally provides the associated control of the at least one monitor, the archiving member and the printer.

In conformity with a further aspect of the invention, the device is characterized in that the user interface is arranged to present computer-controlled instructions to a user, in dependence on the patient-specific data and the examination-specific data, that is, instructions tuned to the progress of the predetermined examination program.

It is thus ensured that the presetting as well as the further execution of an examination program can be performed completely under the control of the computer, the user being given each time instructions concerning the further operations required for this purpose. Making mistakes during the examination can thus be very effectively counteracted.

The invention will be described in detail hereinafter with reference to a non-limitative embodiment and the accompanying drawing. In the drawing.

In order to carry out, for example, a series of X-ray examinations by means of a self-contained X-ray examination apparatus, first the set of patients 1 (see FIG. 1) to be examined has to be defined. Patient-specific data is collected on the patients 1 so as to be input in the computer 6 of the device 5 as shown in FIG. 2. For each patient this information concerns the identity, physical characteristics, such as weight, and the parts of the body to be examined for the relevant patient. This information can be derived, for example, automatically from a hospital information system.

Figure 1:
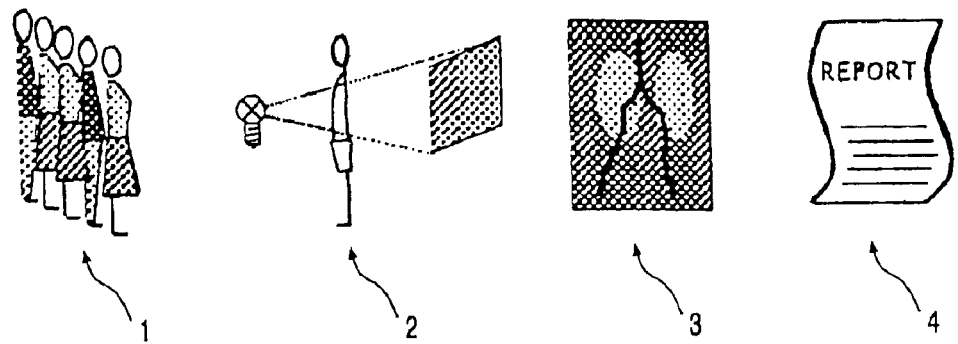
FIG. 1 is a symbolic representation of a number of temporally successive operations which serve to carry out an X-ray analysis on a series of patients.
Figure 2:
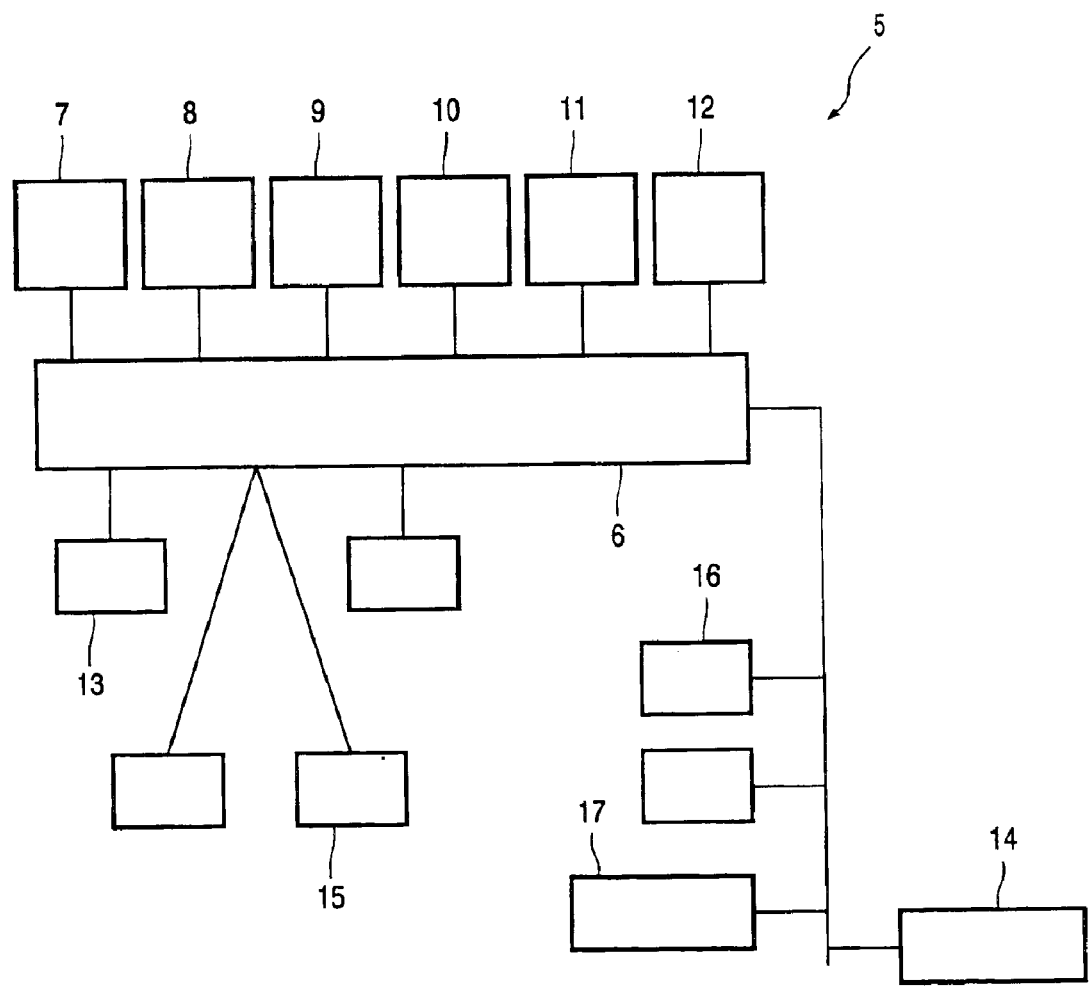
FIG. 2 is a diagrammatic representation of a computer-controlled device in accordance with the invention.

After the patients have been individualized in this manner, the actual examination can be performed for each patient individually in the device as symbolized by the section 2 of FIG. 1.

Inter alia the X-ray source 7 (see FIG. 2) and the examination table 9 are adjusted in dependence on the examination-specific data concerning the relevant patient; these settings may also be dependent on patient-specific data. Subsequently, the relevant part of the body of the patient is examined. The section which is denoted by the reference numeral 3 in FIG. 1 symbolizes the analysis by the user of the images thus obtained. There are various possibilities in this respect. For example, comparatively low radiation doses can be used so as to form a fluoroscopic image which enables interactive examination of the patient, that is, an examination for which the settings of, for example, the examination table 9 are adapted during the examination. It is also possible to form a single image which can be reviewed directly on the monitor 12 of the device 5.

The section 4 of the Figure symbolizes that, subsequent to the above real-time reviewing, reporting and archiving are possible by making the image available via a printer 15 as shown in FIG. 2 or by storing the images formed in electronic archives 14.

FIG. 2 shows the above-mentioned components of the installation in a coherent representation. The core of the device 5 for carrying out an X-ray analysis or for forming an X-ray image or a fluoroscopic image as elucidated above comprises a computer 6 whereto the various components of the device are connected. FIG. 2 shows an X-ray source 7, a collimator 8, an examination table 9 and a detector 10 which together constitute the core of the X-ray analysis device. Also shown are an image processing member 11, a monitor 12, a user interface 13, an archiving member 14 and a printer or printers 15; moreover, data links which offer access to, for example, a hospital information system 16 or monitor equipment 17 installed elsewhere may also be connected to the computer 6.

The computer 6 is provided, in a manner known to a person skilled in the art, with a database for the storage of settings for the X-ray source 7 and the examination table 9; the computer 6 is also provided, in a manner which is also known to a person skilled in the art, with a control member for realizing said settings which are stored in the database (for example, see DE-A 19 625 410).

As has already been described, the database of the computer 6 also contains patient-specific data and examination-specific data and the computer 6 is arranged to execute a predetermined examination program in dependence on the data taken up in the database; the control member of the computer 6 the realizes the setting of the various components of the device 5 in dependence on the said patient-specific data and examination-specific data. Such setting concerns not only the setting of the X-ray source 7, of the collimator 8, of the examination table 9 and of the detector 10, but also the operation of the image processing member 11 which processes the images from the detector 10. The control member of the computer 6 also determines the order of and the rate at which the monitor 12 displays the images formed; it also determines the form in which they are displayed and also provides the control of the printer or printers 15 and the archiving system 14. As has already been indicated above, a coupling to a hospital information system 16 is also feasible. On the basis thereof, for example, invoices can be made up directly on the basis of the operations carried out.

For the controlled completion of an examination to be carried out on an individual patient there is also provided a user interface 13 which is arranged to present computer-controlled instructions to a user of the device 5 in dependence on the patient-specific data and the examination-specific data taken up in the database of the computer 6; such instructions are then completely tuned to the execution of the predetermined examination program.

As far as the predetermined examination programs which may be taken up in the computer 6 of the system are concerned, it is desirable to gather such programs in groups in such a manner that application groups are formed for examinations relating to a given part of the body of the patients to be examined. For example, one examination group may relate to the digestive tract, a next examination group to the vascular system, a third examination group to the neurological system and so on.

In each examination group further applications can be distinguished. For example, with respect to the examination group "digestive tract" a distinction can be made as regards the region of the colon, the esophagus, the stomach and so on. For each application of this kind the database of the computer 6 contains associated settings of the X-ray source 7 and possibly of the examination table 9; the presentation via monitors 12 and 17 and the archiving in the archiving member 14 can then also take place automatically in the manner described above. Preferred settings of the various users of the device can also be taken into account.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. A computer-controlled device for forming an X-ray image or a fluoroscopic image comprising:

a computer;

an X-ray source;

a collimator;

an examination table;

a detector;

an image processor;

at least one monitor;

a user interface;

an archiving members;

a printer;

a database for the storage of settings of (1) the X-ray source and of the examination table, and (2) patient-specific data, and (3) examination-specific data;

an examination program executed by the computer to (1) retrieve the patient-specific data and the examination-specific data from the database the and (2) from the patient-specific data and the examination-specific data determine settings for at least the x-ray source, the collimator, the examination table, the image processor, and the archiving member, the control member receiving the determined settings and controlling the x-ray source, the collimator, the examination table, the image processor, and the archiving member, in accordance with the determined settings.

2. The device as claimed in claim 1, wherein the user interface is arranged to present computer-controlled instructions to a user, in dependence on the patient-specific data and the examination-specific data, which instructions are tuned to the execution of the examination program.

3. The device as claimed in claim 1, wherein the image processor generates a real-time image and the examination program determines settings which cause the control member to control the monitor, display the image and the archiving member, and the printer to at least one of print and archive the image.

4. A computer-controlled x-ray or a fluoroscopic imaging system comprising:

system components including at least one of an x-ray source, a collimator, an examination table, a detector, an image processor, at least one monitor, a user interface, an archiving routine, and a printer; and a computer including a database for storing patient-specific data and examination-specific data, the computer being programmed to:

generate examination parameters from the patient-specific data and the examination-specific data stored in the database,
select images for at least one of display, printing, and archiving from the examination-specific data, and in dependence on the examination parameters and the patient-specific data and the examination;
specific data, generating a report which includes the selected images.

5. The device as claimed in claim 1, wherein the patient-specific data contains information concerning an identity, physical features, and parts of a body of a patient to be examined.

6. A computer-controlled device for forming an x-ray image or a fluoroscopic image including:

an x-ray source;

a collimator;

an examination table;

an x-ray detector;

an image processor;

a monitor;

a user interface; and, a computer provided with
a database for storing settings of the x-ray source and of the examination table, the database containing patient-specific data and examination-specific data, the patient-specific data including a patient identity and a body portion to be examined, the examination-specific data including information concerning a time of examination, desired presettings of the X-ray source, the detector, and the examination table, and a selected examination program to be executed, the computer executing an examination program in dependence on the patient-specific data and the examination-specific data in the database, and
a control module which calculates and sets at least the x-ray source, the examination table, and the image processor in accordance with the patient-specific data and the examination-specific data.

* * * * *